US007842724B2

(12) United States Patent
Julian

(10) Patent No.: US 7,842,724 B2
(45) Date of Patent: *Nov. 30, 2010

(54) PHARMACEUTICAL GALLIUM COMPOSITIONS AND METHODS

(75) Inventor: Thomas N. Julian, Annandale, NJ (US)

(73) Assignee: Genta Incorporated, Berkeley Heights, NJ (US)

( * ) Notice: Subject to any disclaimer, the term of this patent is extended or adjusted under 35 U.S.C. 154(b) by 149 days.

This patent is subject to a terminal disclaimer.

(21) Appl. No.: 12/046,128

(22) Filed: Mar. 11, 2008

(65) Prior Publication Data

US 2008/0160103 A1  Jul. 3, 2008

Related U.S. Application Data

(63) Continuation of application No. 11/551,422, filed on Oct. 20, 2006, now Pat. No. 7,354,952.

(60) Provisional application No. 60/733,388, filed on Nov. 4, 2005.

(51) Int. Cl.
*A61K 31/28* (2006.01)
*A61P 35/00* (2006.01)

(52) U.S. Cl. .................... 514/492; 424/DIG. 6; 514/970

(58) Field of Classification Search ........................ None
See application file for complete search history.

(56) References Cited

U.S. PATENT DOCUMENTS

| | | | |
|---|---|---|---|
| 5,196,412 A | 3/1993 | Bradley et al. | |
| 5,258,376 A | 11/1993 | Bernstein | |
| 5,281,578 A | 1/1994 | Bradley et al. | |
| 5,525,598 A | 6/1996 | Collery et al. | |
| 5,574,027 A | 11/1996 | Bernstein | |
| 5,650,386 A | 7/1997 | Leone-Bay et al. | |
| 5,866,536 A | 2/1999 | Leone-Bay et al. | |
| 5,883,088 A | 3/1999 | Bernstein | |
| 5,968,922 A | 10/1999 | Bernstein | |
| 5,998,397 A | 12/1999 | Bernstein | |
| 6,004,951 A | 12/1999 | Bernstein | |
| 6,048,851 A | 4/2000 | Bernstein | |
| 6,087,354 A | 7/2000 | Bernstein | |
| 7,297,794 B2 | 11/2007 | Gscheidner et al. | |
| 7,354,952 B2 * | 4/2008 | Julian | 514/492 |
| 2004/0048777 A1 | 3/2004 | Weidner et al. | |
| 2005/0147662 A1 | 7/2005 | Freeman et al. | |

FOREIGN PATENT DOCUMENTS

| | | |
|---|---|---|
| WO | WO-91/17751 | 11/1991 |
| WO | WO-93/02087 | 2/1993 |
| WO | WO-2006/072070 | 7/2006 |

OTHER PUBLICATIONS

PUBMED online, file MEDLINE, PMID 7903343 (van Leeuwen-Stok et al., Int. J. Radiat. Biol. (1993), vol. 64, No. 6, pp. 749-759), Abstract.*
Collery, P. et al., "Preclinical Toxicology and Tissue Gallium Distribution of a Novel Antitumour Gallium Compound: Tris (8-Quinolinolato) Gallium (III)", *Anticancer Research 16*, (1996),687-691.
Farrar, G. et al., "Tissue Distribution of Gallium Following Administration of the Gallium-Maltol Complex in the Rat: A Model for an Aluminium-Maltol Complex of Neorotoxicological Interest", *Pharmaceutical Sciences Institute, Aston University*, (1988),523-525.
Ho, D. H., et al., "Bioavailability Studies of Tetradentate Schiff-Base Gallium Complexes (Salens)", *Metal Ions in Biiology and Medicine* vol. 4, (1996),369-371.
Chitambar, Christopher R., et al., "Evaluation of Transferrin and Gallium-Pyridoxal Isonicotinoyl Hydrazone as Potential Therapeutic Agents to Overcome Lymphoid Leukemic Cell Resistance to Gallium Nitrate", *Clinical Cancer Research*, vol. 2, (Jun. 1996),1009-1015.
Marathe, D. G., et al., "Physco-chemical Investigation on the Complexes of Gallium (III) with Hydroxy Amino Substituted Carboxylic Acids and Hydroxy Ketones", *Nat. Acad. Sci. Letters*. vol. 7, No. 5, (1984),153-156.
Richardson, D. R., "Cytotoxic Analogs of the Iron(III) Chelator Pyridoxal Isonicotinoly Hydrazone: Effects of Complexation with Copper(II), Gallium(III), and Iron(III) on Their Antiproliferative Activities", *Antimicrobial Agents and Chemotherapy*, (Sep. 1997),2061-2063.
Santos, M. A., et al., "N-Carboxyalkyl Derivatives of 3-Hydroxy-4-Pyridinones: Synthesis, Complexation with Fe(III) and Ga(III) and In Vivo Evaluation", *Journal of Inorganic Biochemistry 92*, (2002),43-54.
Stojiljkovic, Igor et al., "Non-Iron Metalloporphyrins: Potent Antibacterial Compounds That Exploit Haem/Hb Uptake Systems of Pathogenic Bacteria", *Molecular Microbiology*, (1999 31(2)),429-442.
Sun, Yizhen et al., "Indium(III) and Gallium(III) Complexes of Bis(aminoethanethiol) Ligands with Different Denticities: Stabilities, Molecular Modeling, and in Vivo Behavior", *J. Med. Chem.*, (1996, 39),458-470.
Weizman, Haim et al., "1,2-Hopobactin: a hydroxamate analog of enterobactin", *The Royal Society of Chemistry*, (2000),2013-2014.
Thiel, M. et al., "Tris(8-quinolinolato) Gallium(III), a Novel Orally Applied Antitumor Gallium Compound", *Relevance of Tumor Models for Anticancer Drug Development*, (1999, vol. 54),439-443.

(Continued)

*Primary Examiner*—Johann R Richter
*Assistant Examiner*—Frank I Choi
(74) *Attorney, Agent, or Firm*—Diehl Servilla LLC

(57) ABSTRACT

Novel pharmaceutical gallium compositions, including gallium complexes having increased oral bioavailability relative to uncomplexed gallium salts are disclosed. Such compositions are useful in the treatment of conditions and diseases in which inhibition of abnormally increased calcium resorption is desired, including cancer, hypercalcemia, osteoporosis, osteopenia and Paget's disease. Methods for preparation and treatment are also provided.

11 Claims, 1 Drawing Sheet

OTHER PUBLICATIONS

Ambulkar, R. S., et al., "Stepwise Stability Constants of Gallium(III) Complexes with Picolinic Acid and 8-Hydroxyquinoline and its Derivatives", *J. Indian Chem. Soc.* vol. LII, (Apr. 1975),315-317.

Ambulkar, R. S., et al., "Complexes of Ga(III) with Thiomalic, Thiolactic, Thioglycollic, Malic Glycollic, Lactic & Aspartic Acides, & Alanine & Glycine", *Indian Journal of Chemistry* Vo. 14A, (Jun. 1976),424-427.

Arion, Vladimir B., et al., "Synthesis, Structure, Spectroscopic and in Vitro Antitumour Studies of a Novel Gallium(III) Complex with 2-Acetylpyridine N-Dimethylthiosemicarbazone", *Journal of Inorganic Biochemistry 91*, (2002),298-305.

Bernstein, Lawrence R., et al., "Chemistry and Pharmacokinetics of Gallium Maltolate, a Compound with High Oral Gallium Bioavailability", *Metal-Based Drugs* vol. 7, No. 1, (2000),33-47.

PCT/US06/40986 International Search Report, 2 pages.

* cited by examiner

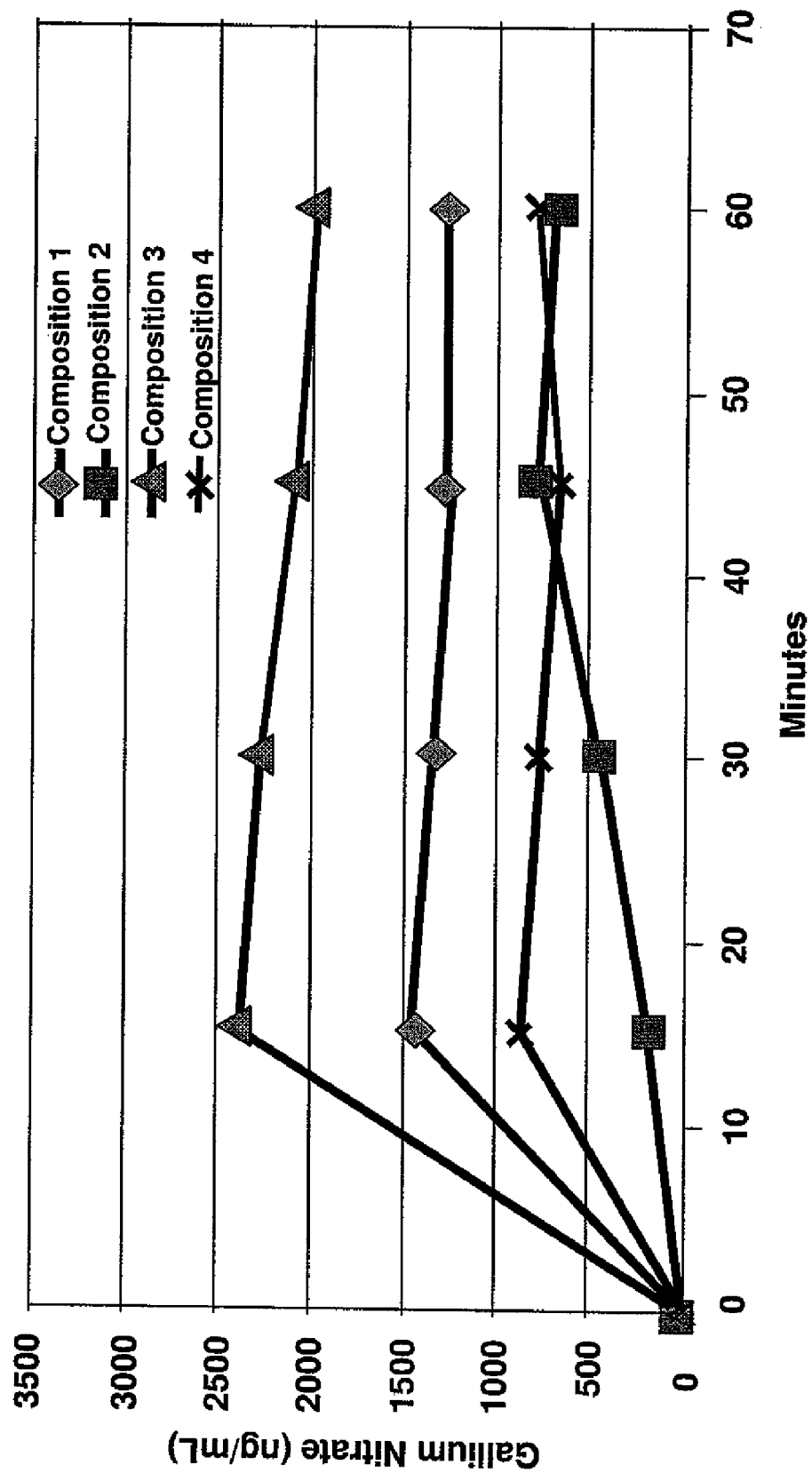

PHARMACEUTICAL GALLIUM COMPOSITIONS AND METHODS

CROSS-REFERENCE TO RELATED APPLICATION

This application is a continuation of U.S. application Ser. No. 11/551,422, filed Oct. 20, 2006, which claims the benefit of priority to U.S. Provisional Application No. 60/733,388, filed Nov. 4, 2005, the disclosures of which are hereby incorporated by reference in their entireties.

FIELD OF THE INVENTION

The present invention relates generally to pharmaceutical gallium compositions, including gallium complexes having increased oral bioavailability relative to uncomplexed gallium salts, and uses therefor.

BACKGROUND OF THE INVENTION

Gallium has demonstrated pharmaceutical value for the treatment of many human and animal disorders, including hypercalcemia, cancer, and especially certain widespread degenerative or metabolic bone diseases such as osteoporosis and Paget's disease. For example, numerous clinical studies have shown gallium to have antineoplastic activity, as well as the ability to reduce abnormally high bone turnover in Paget's disease (reviewed in Bernstein, Therapeutic Gallium Compounds, in Metallotherapeutic Drugs and Meta-Based Diagnostic Agents: The Use of Metals in Medicine 259-277 (Gielen and Tiekink eds., 2005)). Gallium is currently approved for use in the United States as a citrate-chelated gallium nitrate solution for intravenous infusion (Ganate®) to treat hypercalcemia of malignancy.

In spite of its established utility, however, the use of gallium in the treatment of such diseases is hampered by the fact that ionic gallium, in the form of salts such as nitrate and chloride, lacks high bioavailability when delivered orally. The low bioavailability of orally delivered gallium salts requires that either impractically large doses of orally delivered gallium be administered to the patient or that the gallium be administered via non-oral means (e.g., intravenous delivery). At present, the oral delivery of such gallium salts is not believed to be practical with chronic conditions such as osteoporosis and Paget's disease due to their low bioavailability.

Efforts have been made to increase the bioavailability of orally administered gallium, particularly through chemical complexing. Several gallium complexes have been identified that demonstrate increased oral bioavailability, including, e.g., gallium maltoate (see, e.g., Bernstein et al., Metal-Based Drugs 7:33-47 (2000); U.S. Pat. Nos. 5,258,376; 5,574,027; 5,883,088; 5,968,922; 5,998,397; 6,004,951; 6,048,851; 6,087,354)) and gallium 8-quinolinolate (see, e.g., Collery et al., Anticancer Res. 16:687-692 (1996); U.S. Pat. No. 5,525,598; European Patent No. EP 0 599 881; International Application No. PCT/EP92/01687). Other therapeutic gallium complexes are described in, e.g., Arion et al., J. Inorg. Biochem. 91:298-305 (2002); Chitambar et al., Clin. Cancer Res. 2:1009-1015 (1996); Stojilkovic et al., Mol. Microbiol. 31:429-442 (1999); U.S. Pat. Nos. 5,196,412; 5,281,578; and International Application No. PCT/US91/03599. There is a continuing need, however, for the development of new pharmaceutical gallium compositions, particularly gallium complexes having enhanced oral bioavailability.

SUMMARY OF THE INVENTION

Embodiments of the present invention provide novel pharmaceutical gallium compositions and methods for treating conditions and diseases in which inhibition of abnormally increased calcium resorption is desired. More particularly, embodiments of the present invention further provide novel gallium complexes having increased oral bioavailability and methods of treating conditions and diseases such as cancer, hypercalcemia, osteoporosis, osteopenia, and Paget's disease using such complexes.

Accordingly, one aspect of the present invention is directed to a gallium complex comprising gallium and a compound represented by structural formula I:

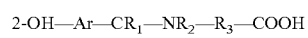

2-OH—Ar—CR$_1$—NR$_2$—R$_3$—COOH wherein 2-OH—Ar is an optionally substituted 2-hydroxyaryl;

R$_1$ is —OH or =O;

R$_2$ is hydrogen, hydroxyl or an optionally substituted C$_1$-C$_4$ alkyl, C$_1$-C$_4$ alkoxy, or C$_2$-C$_4$ alkenyl; and R$_3$ is an optionally substituted aryl, heteroaryl, cycloalkyl, heterocyclyl, C$_1$-C$_{24}$ alkyl, C$_2$-C$_{20}$ alkenyl, C$_2$-C$_{20}$ alkynl, C$_1$-C$_{10}$ alkylaryl, C$_1$-C$_{10}$ arylalkyl, C$_2$-C$_{10}$ alkenylaryl, C$_2$-C$_{10}$ arylalkenyl, C$_2$-C$_{10}$ alkynylaryl or C$_2$-C$_{10}$ arylalkynyl, which optionally is interrupted by O, N, S or any combination thereof.

Another aspect of the present invention is directed to a method for preparing a gallium complex comprising reacting gallium with a compound represented by structural formula I under conditions sufficient to form said gallium complex. In some embodiments, the gallium complex is prepared prior to administration to a patient. In other embodiments, the gallium complex is formed in situ following administration.

Another aspect of the present invention is directed to a pharmaceutical composition for administering gallium to a patient comprising gallium, a compound represented by structural formula I, and at least one pharmaceutically acceptable excipient. In some embodiments, the gallium and the compound represented by structural formula I are complexed prior to administration of the composition. In other embodiments, a gallium complex is formed in situ following administration of the composition.

Another aspect of the present invention is directed to a method for administering gallium to a patient comprising administering to said patient a pharmaceutical composition comprising gallium, a compound represented by structural formula I and at least one pharmaceutically acceptable excipient. In some embodiments, the gallium and the compound represented by structural formula I are complexed prior to administration of the composition. In other embodiments, a gallium complex is formed in situ following administration of the composition.

Another aspect of the present invention is directed to a method for treating a condition or disease characterized by excessive bone resorption comprising administering to a patient in need of such treatment a therapeutically effective amount of gallium and a compound represented by structural formula I. In some embodiments, the gallium and the compound represented by structural formula I are in a single dosage pharmaceutical composition. In further embodiments, the gallium and the compound represented by structural formula I are complexed prior to oral administration. In other embodiments, complexing occurs following oral administration.

Another aspect of the present invention is directed to a method for increasing the oral bioavailability of gallium comprising complexing gallium with a compound represented by structural formula I. In some embodiments, the gallium and the compound represented by structural formula I are complexed prior to oral administration. In other embodiments, complexing occurs following oral administration.

BRIEF DESCRIPTION OF THE FIGURE

The FIGURE shows a graph of bioavailability of gallium nitrate over time.

DETAILED DESCRIPTION OF THE INVENTION

The present invention relates to gallium complexes comprising gallium and a compound represented by structural formula I, wherein $R_1$, $R_2$ and $R_3$ are as defined above. The compounds represented by structural formula I can be administered as racemic mixtures or enantiomerically pure compounds.

One group of preferred compounds for use in the gallium complexes of the present invention are compounds represented by structural formula I wherein 2-OH—Ar is 2-hydroxyphenyl optionally substituted at the 4-position, $R_1$ is =OH, $R_2$ is H and $R_3$ is an optionally substituted $C_1$-$C_{24}$ alkyl.

Accordingly, one group of preferred compounds for use in the gallium complexes of the present invention are compounds represented by the formula:

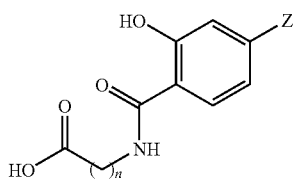

wherein Z is H or halo and n is 3-11.

Particularly preferred compounds of this group include those wherein Z is H and n is 7, wherein Z is H and n is 9 and wherein Z is Cl and n is 3.

Another group of preferred compounds for use in the gallium complexes of the present invention are compounds represented by structural formula I wherein 2-OH—Ar is 2-hydroxyphenyl, $R_1$ is HO—, $R_2$ is H and $R_3$ is an optionally substituted $C_1$-$C_{24}$ alkyl.

Accordingly, another group of preferred compounds for use in the gallium complexes of the present invention are compounds represented by the formula:

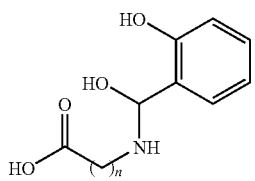

wherein n is 3-11.

Particularly preferred compounds of this group include those wherein n is 9.

Except where stated otherwise, the following definitions apply throughout the present specification and claims. These definitions apply regardless of whether a term is used by itself or in combination with other terms. For example, the definition of "alkyl" applies to "alkyl" as well as to the "alkyl" portions of "alkoxy", "alkylamino" etc.

"Patient" includes both human and other animals.

"Mammal" means humans and other mammalian animals.

The term "treating" or "treatment" of a state, disorder, disease or condition as used herein means: (1) preventing or delaying the appearance of clinical symptoms of the state, disorder, disease or condition developing in a mammal that may be afflicted with or predisposed to the state, disorder, disease or condition but does not yet experience or display clinical or subclinical symptoms of the state, disorder or condition, (2) inhibiting the state, disorder, disease or condition, i.e., arresting or reducing the development of the disease or at least one clinical or subclinical symptom thereof, or (3) relieving the disease, i.e., causing regression of the state, disorder or condition or at least one of its clinical or subclinical symptoms. The benefit to a subject to be treated is either statistically significant or at least perceptible to the patient and/or to the physician.

"Effective amount" and "therapeutically effective amount" mean the amount of a compound that, when administered to a mammal for treating a state, disorder, disease or condition, is sufficient to effect such treatment. The effective amount or therapeutically effective amount will vary depending on the compound, the disease and its severity, and the age, weight, physical condition and responsiveness of the individual to be treated.

"Delivering" and "administering" means providing a therapeutically effective amount of an active ingredient to a particular location or locations within a host causing a therapeutically effective blood concentration of the active ingredient at the particular location or locations. This can be accomplished, e.g., by local or by systemic administration of the active ingredient to the host.

The term "coadministration" encompasses administration of a first and second agent (e.g., gallium and a compound represented by structural formula I) in an essentially simultaneous manner, such as in a single dosage form, e.g., a capsule or tablet having a fixed ratio of first and second amounts, or in multiple dosage forms for each. The agents can be administered in a sequential manner in either order. When coadministration involves the separate administration of each agent, the agents are administered sufficiently close in time to have the desired effect (e.g., complex formation).

"Pharmaceutically acceptable" means those active agents, salts and esters, and excipients which are, within the scope of sound medical judgment, suitable for use in contact with the tissues of humans and lower animals without undue toxicity, irritation, allergic response and the like, commensurate with a reasonable benefit/risk ratio, and effective for their intended use.

"A condition or disease characterized by excessive bone resorption" means any state, disorder, disease or condition which is characterized at least in part by excessive calcium resorption from bone, including, but not limited to, cancer, such as Non-Hodgkin's lymphoma, hypercalcemia, osteoporosis, osteopenia, Paget's disease, malignant bone disease, bone degeneration due to hyperparathyroidism and tissue wounds.

"Alkyl" means an aliphatic hydrocarbon group, which may be straight or branched and comprising about 1 to about 24 carbon atoms in the chain. Preferred alkyl groups contain about 1 to about 12 carbon atoms in the chain. Branched means that one or more lower alkyl groups such as methyl, ethyl or propyl, are attached to a linear alkyl chain. "Lower alkyl" means an alkyl group having about 1 to about 6 carbon atoms in the chain, which may be straight or branched. Non-limiting examples of suitable alkyl groups include methyl, ethyl, n-propyl, isopropyl, n-butyl, and t-butyl.

"Alkenyl" means an aliphatic hydrocarbon group comprising at least one carbon-carbon double bond and which may be straight or branched and comprising about 2 to about 20 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means an alkenyl group having about 2 to about 6 carbon atoms in the chain, which may be straight or branched. Non-limiting examples of suitable alkenyl groups include ethenyl, propenyl, n-butenyl, and 3-methylbut-2-enyl.

"Alkynyl" means an aliphatic hydrocarbon group comprising at least one carbon-carbon triple bond and which may be straight or branched and comprising about 2 to about 20 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means an alkynyl group having about 2 to about 6 carbon atoms in the chain, which may be straight or branched. Non-limiting examples of suitable alkynyl groups include ethynyl, propynyl and 2-butynyl.

The "alkyl", "alkenyl" and "alkynyl" can be optionally substituted by replacing an available hydrogen on the chain by one or more substituents, which may be the same or different.

"Alkylene" means an alkanediyl group commonly having free valences on two carbon atoms. Non-limiting examples include methylene, ethylene, propylene and the like.

"Aryl" means an aromatic monocyclic or multicyclic ring system comprising about 6 to about 14 carbon atoms, preferably about 6 to about 10 carbon atoms. Non-limiting examples of suitable aryl groups include phenyl and naphthyl. The aryl group can be optionally substituted by replacing an available hydrogen on the ring with one or more substituents, which may be the same or different. The "aryl" group can also be substituted by linking two adjacent carbons on its aromatic ring via a combination of one or more carbon atoms and one or more oxygen atoms such as, for example, methylenedioxy, ethylenedioxy, and the like.

"Arylene" means a bivalent group derived from an aromatic hydrocarbon by removal of a hydrogen atom from two ring carbon atoms. Non-limiting examples include phenylene and the like.

"Alkylenedioxy" means a combination of one or more carbon atoms and one or more oxygen atoms such as the following non-limiting examples that include methylenedioxy, ethylenedioxy, and the like.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by replacing an available hydrogen on the ring by one or more substituents, which may be the same or different. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrrolyl, triazolyl, and the like.

"Heteroarylene" means a bivalent group derived from a heterocyclic aromatic compound by removal of a hydrogen atom from two ring carbon atoms such as, for example, the bivalent group derived from pyridine, pyrrole and the like.

"Arylalkyl" means an aryl-alkyl-group in which the aryl and alkyl are as previously described. Preferred arylalkyls comprise a lower alkyl group. Non-limiting examples of suitable arylalkyl groups include benzyl, 2-phenethyl and a naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl groups is tolyl. The bond to the parent moiety is through the aryl.

"Arylalkenyl" means an aryl-alkenyl-group in which the aryl and alkenyl are as previously described. Preferred arylalkenyls comprise a lower alkenyl group. The bond to the parent moiety is through the alkenyl.

"Alkenylaryl" means an alkenyl-aryl-group in which the alkenyl and aryl are as previously described. Preferred alkenylaryls comprise a lower alkyl group. The bond to the parent moiety is through the aryl.

"Arylalkynyl" means an aryl-alkynyl-group in which the aryl and alkynyl are as previously described. Preferred arylalkynyls comprise a lower alkenyl group. The bond to the parent moiety is through the alkynyl.

"Alkynylaryl" means an alkynyl-aryl-group in which the alkynyl and aryl are as previously described. Preferred alkynylaryls comprise a lower alkyl group. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted by replacing an available hydrogen on the ring by one or more substituents, which may be the same or different. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl-alkyl-group in which cycloalkyl and alkyl are as previously defined. Non-limiting examples of a suitable cycloalkylalkyl group includes cyclopropylmethyl. The bond to the parent moiety is through the alkyl.

"Alkoxy" means an alkyl-O— group in which the alkyl group is as previously described. Non-limiting examples of suitable alkoxy groups include methoxy, ethoxy, n-propoxy and isopropoxy. The alkyl group is linked to an adjacent moiety through the ether oxygen.

"Halo" means fluoro, chloro, bromo or iodo groups. Preferred are fluoro, chloro or bromo, and more preferred are fluoro and chloro.

"Halogen" means fluorine, chlorine, bromine or iodine. Preferred are fluorine, chlorine or bromine, and more preferred are fluorine and chlorine.

"Haloalkyl" means an alkyl as defined above wherein one or more hydrogen atoms on the alkyl is replaced by a halo group defined above.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted by replacing an available hydrogen on the ring by one or more substituents, which may be the same or different. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by replacing an available hydrogen on the ring by one or more substituents, which may be the same or different. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, tetrahydrothiophenyl, morpholinyl and the like.

"Arylcycloalkenyl" means a group derived from a fused aryl and cycloalkenyl as defined herein by removal of a hydrogen atom from the cycloalkenyl portion. Preferred arylcycloalkenyls are those wherein aryl is phenyl and the cycloalkenyl consists of about 5 to about 6 ring atoms. The arylcycloalkenyl can be optionally substituted by replacing an available hydrogen on the ring by one or more substituents, which may be the same or different. Non-limiting examples of suitable arylcycloalkenyls include 1,2-dihydronaphthalene, indene, and the like. The bond to the parent moiety is through a non-aromatic carbon atom.

"Heteroarylalkyl" means a heteroaryl-alkyl-group in which the heteroaryl and alkyl are as previously described. Preferred heteroaralkyls contain a lower alkyl group. Non-limiting examples of suitable heteroarylalkyl groups include pyridylmethyl, 2-(furan-3-yl)ethyl and quinolin-3-ylmethyl. The bond to the parent moiety is through the alkyl.

"Heteroarylalkenyl" means an heteroaryl-alkenyl-group in which the heteroaryl and alkenyl are as previously described. Preferred heteroarylalkenyls contain a lower alkenyl group. Non-limiting examples of suitable heteroarylalkenyl groups include 2-(pyrid-3-yl)ethenyl and 2-(quinolin-3-yl)ethenyl. The bond to the parent moiety is through the alkenyl.

"Alkoxyalkyl" means an alkoxy-alkyl-group in which alkyl and alkoxy are as previously defined. Non-limiting examples of suitable alkoxyalkyl groups include methoxymethyl, ethoxymethyl, methoxyethyl and ethoxyethyl.

"Aryloxyalkyl" means an aryloxy-alkyl-group in which aryl and alkoxy are as previously defined. Non-limiting examples of suitable aryloxyalkyl groups include benzoxymethyl, substituted aryloxymethyl, benzoxyethyl and substituted aryloxyethyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. P referred acyls contain a lower alkyl. Non-limiting examples of suitable acyl groups include formyl, acetyl, propanoyl, 2-methylpropanoyl, and cyclohexanoyl.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Alkylamino" means an —NH$_2$ or —NH$_3^+$ group in which one or more of the hydrogen atoms on the nitrogen is replaced by an alkyl group as defined above.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Arylalkylthio" means an arylalkyl-S— group in which the aralkyl group is as previously described. Non-limiting example of a suitable arylalkylthio group is benzylthio. The bond to the parent moiety is through the sulfur.

"Alkylcarbonyl" means an alkyl group defined earlier linked to an adjacent moiety through a carbonyl. A non-limiting example of a suitable alkylcarbonyl group is methylcarbonyl.

"Alkoxycarbonyl" means an alkoxy group defined earlier linked to an adjacent moiety through a carbonyl. A non-limiting example of a suitable alkoxycarbonyl group is methoxycarbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylalkoxycarbonyl" means an arylalkyl-O—C(O)— group. A non-limiting example of a suitable arylalkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Arylsulfonyl" means an aryl-S(O$_2$)— group. The bond to the parent moiety is through the sulfonyl.

"Arylsulfinyl" means an aryl-S(O)— group. The bond to the parent moiety is through the sulfinyl.

The term "optionally substituted" means optional substitution with one or more groups, radicals or moieties (i.e., "substituents"), which can be the same or different. Representative substituents include, but are not limited to, any of the substituents described above, particularly halo, alkyl, cycloalkyl, aryl, hydroxy, amino and carboxy.

The term "complex" is intended to encompass a structure formed by the interaction between two or more agents (e.g., gallium and a compound of structural formula I). Such interaction can be via chemical interaction, such as, e.g., covalent, ionic, or secondary bonding (e.g., hydrogen bonding), and the like, or via physical interaction, such as, e.g., encapsulation, entrapment, and the like. The complex can be formed prior to administration to a patient or may form in situ (e.g., the gut) following administration of uncomplexed agents.

The term "composition" is intended to encompass a product comprising the specified ingredients in the specified amounts, as well as any product which results, directly or indirectly, from combination of the specified ingredients in the specified amounts.

Solvates of the compounds of the present invention are also contemplated herein. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds represented by structural formula I may form salts which are also within the scope of this invention. Reference to a compound represented by structural formula I herein is understood to include reference to salts thereof, particularly pharmaceutically acceptable salts thereof, unless otherwise indicated. The term "salt(s)", as employed herein, denotes acidic salts formed with inorganic and/or organic acids, as well as basic salts formed with inorganic and/or organic bases. In addition, when a compound represented by structural formula I contains both a basic moiety, such as, but not limited to, a pyridine or imidazole, and an acidic moiety, such as, but not limited to a carboxylic acid, zwitterions ("inner salts") may be formed and are included within the term "salt(s)" as used herein. Pharmaceutically acceptable salts are preferred, although other salts are also useful. Salts of the compounds represented by structural formula I may be formed, for example, by reacting such as compound with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates, tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds represented by structural formula I, and salts and solvates thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts and solvates of the compounds), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" and the like, is intended to equally apply to the salt and solvate of enantiomers, stereoisomers, rotamers, tautomers or racemates of the inventive compounds.

All polymorphs of the gallium complexes disclosed herein, including amorphous forms, are contemplated within the scope of this invention.

When any variable (e.g., aryl, heterocycle, $R_2$, etc.) occurs more than one time in any constituent or in structural formula I, its definition on each occurrence is independent of its definition at every other occurrence. Also, combinations of substituents and/or variables are permissible only if such combinations result in stable compounds.

Applicants have identified a number of compounds represented by structural formula I that can be used to prepare the gallium complexes of the present invention. Such compounds can be synthesized from commercially available starting materials, such as, e.g., aminocaprylic acid, aminocaproic acid, aminobutyric acid and 4-chlorosalicylic acid, using well-known methods described in, e.g., U.S. Pat. Nos. 5,650,386 and 5,866,536 and U.S. Patent Publication No. 2004/0048777. The length of the aliphatic chains present on the compounds represented by structural formula I may or may not affect cell membrane permeability.

The gallium complexes of the present invention can be prepared prior to administration to a patient in need of gallium treatment by reacting gallium with one or more compounds represented by structural formula I. The gallium will typically be in the form of a gallium ion. The gallium ions can be derived from a gallium salt, such as, e.g., gallium chloride, gallium nitrate, gallium citrate or gallium sulfate. The reaction can be effected in a suitable mutual solvent, including water where appropriate. If desired, however, an organic solvent or an aqueous/organic solvent mixture may be used to effect complexation. Suitable organic solvents may include, e.g., methanol, ethanol, chloroform and mixtures thereof.

The complexing reaction is generally rapid and will usually have proceeded substantially to completion after about 5 min to about 60 min at room temperature, although longer reaction times and lower temperatures may be necessary. In general, following separation of any unreacted reagents or undesired by-products by e.g., ion exchange or gel filtration chromatography, the reaction mixture may be evaporated or freeze dried to yield the solid gallium complex. The gallium complex may, if desired, be recrystallized from a suitable solvent, such as, e.g., water, alcohols such as methanol and ethanol, ether, acetone, chloroform and mixtures containing such solvents. The formation and purity of the gallium complexes can be measured by several methods well known to those skilled in the art, including e.g., NMR spectroscopy, IR spectroscopy, UV/visible light spectroscopy TLC, HPLC, mass spectrometry, and X-ray diffraction analysis.

The gallium complexes of the present invention can also be formed in situ, e.g., in the gut, following either administration or coadministration of the uncomplexed constituents. For example, gallium and a compound represented by structural formula I can be included in a single dosage form and administered to a patient in need of gallium treatment, where the two constituents are allowed to complex in the higher pH of the intestinal tract. Alternatively, the gallium and a compound represented by structural formula I can be included in separate dosage forms and coadministered substantially simultaneously such that complexing occurs in situ.

Although the complexes of the present invention are described primarily in reference to gallium, one skilled in the art will recognize that other metal ions (both radioisotopic and non-radioisotopic) can be complexed using the compounds represented by structural formula I. For example, the compounds represented by structural formula I can be used to enhance the absorption of nutritional metal ions, such as, e.g., Ca, Sr, Mg, Cr, Zn, Au, Ag, Fe, Ni, Cu, etc. The compounds represented by structural formula I can also be used to administer therapeutic metal ions, such as, e.g., Au, Ag, Pt, Zn, Ca, Fe, Mg, Sr, Co, etc. In addition, the compounds represented by structural formula I can be used to deliver diagnostic metal ions, such as, e.g., Ti, Tc, Sr, Ln, Gd, etc. The ion-to-compound stochiometry will vary depending upon the charge of the metal ion, the electron density and donating potential of the formula I compound, the steric effects of both the metal ion and the formula I compound, etc.

In addition to delivery of therapeutic, nutritional and diagnostic metal ion delivery, the compounds represented by structural formula I can also be used as scavengers to remove unwanted metal ions, such as e.g., Pb, Al, Cd, Ag, Cu, Sr, Ra, Po, etc., from body tissue or blood.

As described in the Examples below, Applicants have discovered that certain complexes of gallium with compounds represented by structural formula I exhibit increased oral bioavailability relative to uncomplexed gallium salts. Using the methods described in the Examples below, those skilled in the art can readily identify other compounds represented by structural formula I that can be used form gallium complexes exhibiting increased oral bioavailability. As such, these gallium complexes (and others not necessarily exhibiting increased oral bioavailability) have utility in the treatment of diseases and conditions characterized by excessive bone resorption, such as, e.g., cancer, hypercalcemia, osteoporosis, osteopenia, Paget's disease, malignant bone disease, bone degeneration due to hyperparathyroidism and tissue wounds.

In the treatment of these and other diseases, a therapeutically effective amount of gallium is administered to a patient in need of such treatment. The gallium can be administered in the form of a pharmaceutical composition. Although the gallium compositions of the present invention are particularly suited to oral delivery, other suitable administration routes include, but are not limited to, e.g., nasal, rectal, topical, transdermal, subcutaneous, intravenous, intraarterial, intramuscular, intraventricular, intraarticular, intraperitoneal, and intrathecal.

For the treatment of various forms of cancer, especially malignant tumors, the gallium may comprise radioactive gallium, such as, e.g., gallium-67, which is administered at the site of the tumor. Complexes comprising radioactive gallium may also be used as radiodiagnostic agents to detect the presence of tumors and the like. Typically, from about 100 mg to about 1000 mg of gallium is administered for such purposes, from which the administration of the gallium complexes or compositions of the present invention can be extrapolated.

For gallium complexes prepared prior to administration, a gallium composition can comprise a gallium complex in combination with at least one pharmaceutically acceptable excipient. If the gallium complex is formed in situ, a gallium composition can comprise gallium, a compound represented by structural formula I and at least one pharmaceutically acceptable excipient. The molar ratio of gallium to the compound represented by structural formula I in these compositions (whether complexed or not) is preferably from about 1:1 to about 1:10, more preferably from about 1:2 to about 1:5, and even more preferably about 1:3.

Alternatively, for in situ complex formation, two separate compositions can be used for administration, one comprising gallium in combination with at least one pharmaceutically acceptable excipient and the other comprising a compound represented by structural formula I in combination with at least one pharmaceutically acceptable excipient. Again, the molar ratio of gallium to the compound represented by structural formula I in these compositions is preferably from about 1:1 to about 1:10, more preferably from about 1:2 to about 1:5, and even more preferably about 1:3.

The particular pharmaceutical excipient(s) chosen, as well as the form of the composition, will depend at least in part on the desired administration route. Examples of pharmaceutically acceptable excipients and methods of manufacture for various compositions are well known in the art may be found in, e.g., Remington's Pharmaceutical Sciences, (Gennaro ed., 20th ed. 2000).

For example, when used for oral administration, which is preferred, the gallium composition will preferably be in solid tablet, capsule, caplet or dragee form incorporating a solid excipient, such as, e.g., starch, lactose, dextran or magnesium strearate. The gallium composition can also be in the form of a solution, suspension or emulsion incorporating a liquid excipient, such as, e.g., water, propylene glycol, polyethylene glycol, sorbitol, maltitol, sucrose or a pharmaceutically acceptable buffer, such as phosphate or carbonate buffer.

For oral administration of a gallium complex prepared prior to administration, one or more of several approaches may be employed to avoid or reduce exposure of the complex to the acidic conditions of the stomach and allow release of the complex in the intestine, thereby increasing delivery of gallium to the bloodstream. For example, an excess of the free compound represented by structural formula I used to form the gallium complex (or a similar compound) can be included in the pharmaceutical composition to shift the equilibrium to the complexed state within the stomach.

Another approach is to formulate the pharmaceutical composition in a delayed release form such that at least some of the gallium complex is not released until the intestinal tract is reached. One method is to formulate the gallium complex with a gel, preferably a hydrogel, such as, e.g., a polymerized polyethylene glycol hydrogel, that adsorbs the complex and releases it only very slowly in the stomach, allowing the majority of complex to be released in the intestine. The preparation of such delayed release formulations, particularly those involving hydrogels, is well known in the art.

Alternatively, the gallium complex can be encapsulated such that the release of the complex is prevented or inhibited until the higher pH of the intestinal tract is reached. For example, the gallium complex can be microencapsulated within liposomes, preferably phospholipids, that do not dissociate under the acidic conditions of the stomach, but which will release the complex in the higher pH of the intestine.

A particularly preferred encapsulation approach is the use of an enteric coating to inhibit or prevent release of the gallium complex until a pH greater than about 5 or 6 is reached. Preferred materials for enteric coating include, but are not limited to, e.g., cellulose acetate phthalate, hydroxypropyl methylcellulose phthalate, poly(vinyl acetate phthalate), hydroxypropyl methylcellulose acetate succinates, poly (meth)acrylates and cellulose acetate phthalate/diethylphthalate. Since the pH of the stomach is higher after a meal, it may be advantageous to administer the gallium complex at such time, whatever oral formulation is used.

The pharmaceutical compositions described herein generally comprise from about 1 to about 99 weight percent of gallium. Preferably, when a pharmaceutically acceptable excipient is employed in the pharmaceutical compositions of the present invention, the compositions contain from about 1 to about 99 weight percent of the excipient. When the compositions also contain a sufficient amount of a means to inhibit dissociation of a complex under the acidic conditions of the stomach, the material comprising such means is incorporated into the pharmaceutical composition at no more than about 98 weight percent of the composition.

Doses are selected to provide pharmaceutically active plasma gallium concentrations for the treatment of excessive resorption of calcium from bone (e.g., arising from cancer, hypercalcemia, osteoporosis, osteopenia, Paget's disease, etc.), which is established to be about 0.1-5.0 µg/ml, preferably about 0.5-2.0 µg/ml. Such blood levels may be achieved by administering about 0.1-20 grams of gallium daily.

For the treatment of various forms of cancer, including cancer-related hypercalcemia, gallium is typically administered in the range from about 0.25 mg/kg/day to about 10 mg/kg/day, preferably from about 0.5 mg/kg/day to about 5 mg/kg/day, from which the administration of the gallium complexes and compositions of the present invention can be extrapolated. Such doses may be administered as a single unit dose or in a number of smaller doses.

Specific embodiments according to the methods of the present invention will now be described in the following examples. The examples are illustrative only, and are not intended to limit the remainder of the disclosure in any way.

EXAMPLES

Example 1

A complex of gallium and a compound represented by structural formula I (i.e., "complexing agent") is prepared as follows. The complexing agent is dissolved in ethanol and mixed with a simple gallium salt, such as the chloride, nitrate or sulfate, as a solid or a solution in an aqueous or organic solvent, in the presence or absence of monovalent alkali metal or other monovalent cationic salts, and stirred for two hours. The solvent is evaporated off and the residue resuspended in chloroform. The gallium complex in chloroform is washed of excess gallium and counter-ions by extraction with pure water and dried over $Na_2SO_4$. The chloroform solvent is evaporated off and the residue resuspended in excess methanol. The purified gallium complex is crystallized by partial evaporation of the methanol solvent, recovered by filtration, and air-dried or dried under vacuum.

Example 2

A complex of gallium and a compound represented by structural formula I (i.e., "complexing agent") is prepared as follows. The complexing agent is dissolved in pure methanol, pure ethanol, or other pure alcohol, or a suitable alcohol-organic compound solvent mixture such as a 1:1 mixture of methanol/dichloromethane, or a pure organic solvent such as chloroform or other suitable solvent system, and mixed with a gallium salt, such as the chloride, nitrate or sulfate, as a solid or a solution in an aqueous or organic solvent, in the presence or absence of monovalent alkali metal salts, and refluxed for 15 hours. The precipitated gallium complex is filtered, washed in the appropriate solvent system, washed in water, and air-dried or dried under vacuum.

Example 3

A complex of gallium and a compound represented by structural formula I (i.e., "complexing agent") is prepared as follows. The complexing agent is dissolved in water, physiological saline, phosphate buffered saline, cell culture medium, or other physiologically compatible solvent system and mixed with a simple gallium salt, such as the chloride, nitrate or sulfate, as a solid or a solution in an aqueous or organic solvent, in the presence or absence of monovalent alkali metal or other monovalent cationic salts, and allowed to sit until complexes are formed as monitored by UV-visible light spectrophotometry.

Example 4

A complex of gallium and a compound represented by structural formula I (i.e., "complexing agent") is prepared as follows. The complexing agent is dissolved in water, physiological saline, phosphate buffered saline, cell culture medium, or other physiologically compatible solvent system and mixed with a simple gallium salt, such as the chloride, nitrate or sulfate, as a solid or a solution in an aqueous or organic solvent, in the presence or absence of monovalent alkali metal or other monovalent cationic salts, and stirred for 1 hr. The solution is loaded onto a suitable cation-exchange column matrix, such as Bio-Rad AG 50W-X8 or Bio-Rad AG 50W-X4, and washed with a suitable solvent, such as water, to remove excess compound and free gallium and other ions. The gallium complex is eluted from the ion exchange column with a suitable eluant, such as 1 M $NH_4OH/NH_4Cl$, pH 9 or a linear gradient of 0.1 M $NH_4OH$/acetic acid, pH 6.0, to 1 M $NH_4OH$/acetic acid, pH 9.0. Elution of the gallium complex is monitored spectroscopically at a wavelength suitable to detect the complex, such as 220 nm. The eluate is concentrated by a suitable method such as evaporation, and any excess precipitated salt from the concentrated eluant removed by filtration. Excess salts in the concentrated eluate are removed by passage through a suitable gel filtration matrix, such as Sephadex G10. The concentrated eluate is loaded onto the desalting column and then washed and eluted with distilled water. The salt-free eluate is concentrated again by a suitable method, such as evaporation.

Example 5

The formation and purity of the gallium complexes are measured by several common methods.

¹H and ¹³C NMR Spectroscopy

Formation of gallium complexes is confirmed and gallium-compound atomic interactions defined by recording and comparing ¹H and ¹³C NMR spectra, scanned from 20 to 900 MHz, of gallium-compound complexes versus the parent compounds alone in deuterium oxide, deuterated chloroform, or other suitable deuterated solvent according to standard methods using instruments such as Bruker DRX 500 and AM400 NMR spectrometers. Shifts in parts per million of hydrogen and carbon nuclei absorbance relative to the absorbance of tetramethylsilane, or the loss of specific hydroxyl group hydrogen for some compounds, reveals gallium-compound interactions.

IR Spectroscopy

Formation of gallium complexes is confirmed and gallium-compound atomic interactions defined by recording and comparing Fourier Transform infrared spectra (FT-IR) on an instrument such as a Bruker IFS spectrometer. Solid samples of gallium complexes and parent compounds alone are placed between IR window materials such as NaCl, KBr, or other suitable materials and scanned through the IR spectrum. Distinctive shifts vibration frequencies between gallium complexes and free compounds will be observed by changes the absorbance of specific C=C, C=O, C—OH, C—NH, and C=N groups in the presence and absence of gallium.

UV-Visible Light Spectroscopy

Formation of gallium complexes is confirmed by recording and comparing near UV-visible absorption spectra, scanned from 225 to 700 nm using an instrument such as a Cary-1E UV-Vis spectrophotometer and standard 1 cm quartz cuvettes, of the free compounds dissolved in methanol versus the gallium complexes dissolved in water, methanol, or other suitable solvent. Complex formation is indicated by distinct wavelength shifts in absorption minima and maxima, and/or changes in the molar extinction coefficient at absorbance minima and maxima, measured for each gallium complex versus the parent compounds alone.

Thin-Layer Chromatography

The purity of the gallium complexes is evaluated by thin-layer chromatography on silica gel plates using a suitable solvent phase, such as 80% methanol/20% water, and a detection system such as a 10% ferric chloride spray. Shifts in position of spots on the TLC plates and the number of spots per sample will indicate gallium complexes and free compounds.

High Performance Liquid Chromatography

The formation and purity of the gallium complexes is evaluated by HPLC analysis on a suitable column such as a Lichrosorb RP8, 10 micron bead diameter, using a suitable solvent gradient such as water, trifluoroacetic acid, methanol, or suitable mixtures. The eluate is monitored by absorbance at a suitable wavelength such as 220 nanometers.

Mass Spectometry

The formation of gallium complexes is confirmed by measuring the mass spectra on an instrument such as a Finnigan MAT 90 mass spectrometer. Complex formation is indicated by shifts in mass peaks of complexes relative to free parent compounds.

X-Ray Structure Analysis

The X-ray structures of gallium complexes are determined by performing X-ray diffraction pattern determinations on an instrument such as a Nonius KappaCCD diffractometer. Crystallographic structures are solved using appropriate software packages such as DENZO-SMN, SORTAV, SHELXS-97, SHELXL-97, and presented using graphics software such as SCHAKAL. Formation of gallium complexes is indicated by alterations in the fundamental crystal structure space groups and/or differences in diffraction patterns and in final solved structures locating the position of the gallium ions relative to the compound and other ions that might be incorporated into the gallium complex crystals relative to the crystals formed by the compounds alone.

REFERENCES

Snow, Biochem. J. 115:199-205 (1969), Adjimani et al., J. Bacteriol. 169:3664-3668 (1987), Sharman et al., Biochem. J. 305:187-196 (1995), Richardson, Antimicrob. Agents Chemother. 41:2061-2063 (1997), Albrecht et al., Proc. Natl. Acad. Sci. USA 99:4867-4872 (2002), Filik et al., Anal. Sci. 18:955-957 (2002).

Example 6

A tablet dosage form of gallium nitrate and a compound represented by structural formula I (i.e., "complexing agent") is prepared as follows. Gallium nitrate hydrate is weighed and then de-lumped by screening through an appropriate sized screen or mill. The sized material is then wet granulated in a higher shear granulator with a binder solution and a diluent. The wet granulation is then dried in a tray dryer to a defined water content. The gallium nitrate granulation is then screened and blended with the complexing agent, a binder/diluent, lubricant, disintegrant and glidant. Blending is then performed in a twin shell or bin blender. The final blend is then compressed into tablets using a standard high speed rotary tablet press. The tablets, having appropriate pharmaceutical characteristics such as hardness, friability and dissolution can then be film coated or enteric coated using a pan coater or a fluidized bed coater.

Example Tablet Formulation:

| Ingredient | Function | Percent (w/w) | Weight per tablet (mg) | Batch weight - 10,000 tablets (gm) |
| --- | --- | --- | --- | --- |
| Gallium nitrate hydrate | Active agent (gallium) | 24 | 180 | 1800 |
| Pregelatinized starch | Intra-granular binder | 5 | 37.5 | 375 |
| Water | Granulation aide (removed during drying) | | | |
| Lactose | Diluent | 14.8 | 111 | 1110 |
| Complexing agent | Absorption enhancer/carrier | 40 | 300 | 3000 |

| Ingredient | Function | Percent (w/w) | Weight per tablet (mg) | Batch weight - 10,000 tablets (gm) |
|---|---|---|---|---|
| Microcrystalline Cellulose | Diluent/disintegrant | 10 | 75 | 750 |
| Sodium Starch glycolate | Disintegrant | 4 | 30 | 300 |
| Magnesium Stearate | Lubricant | 2 | 15 | 150 |
| Colloidal silicon dioxide | Glidant | 0.2 | 1.5 | 15 |
| | Total | 100 | 750 | 7500 |

Example 7

The plasma levels of gallium in rats were determined at various time points up to 1 hr following administration of various gallium compositions. Composition 1 was gallium nitrate (5.5 mg/kg) administered intravenously. Composition 2 was gallium nitrate (55 mg/kg) administered orally. Composition 3 was gallium nitrate (55 mg/kg) in combination with a compound according to the present invention (200 mg/kg) having a carrier of the formula

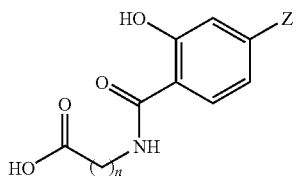

where n=7 and Z=H, administered orally. Composition 4 was gallium nitrate (55 mg/kg) in combination with a compound (200 mg/kg) having the structure

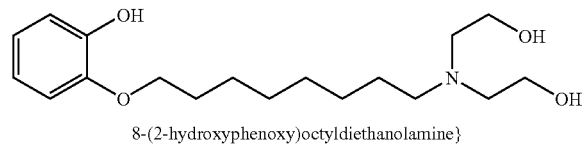

8-(2-hydroxyphenoxy)octyldiethanolamine} administered orally.

As shown in the FIGURE, Composition 3 exhibited greater oral bioavailability than gallium nitrate (GaNO$_3$) alone administered orally (Composition 2). Composition 3 also exhibited substantially greater oral bioavailability than Composition 4. Overall, plasma levels of gallium following administration of Composition 4 were comparable to levels produced following oral administration of GaNO$_3$ alone (Composition 2). On average, the oral administration of gallium in combination with a compound according to the present invention increased the bioavailability of gallium from about 3-fold to about 10-fold compared to the oral administration of gallium alone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

What is claimed:

1. A method for treating cancer comprising administering to a patient in need of such treatment a therapeutically effective amount of gallium and a compound represented by structural formula I:

$$2\text{-OH}-\text{Ar}-\text{CR}_1-\text{NR}_2-\text{R}_3-\text{COOH} \qquad \text{I}$$

wherein 2-OH—Ar is an optionally substituted 2-hydroxyaryl;

R$_1$ is —OH or =O;

R$_2$ is hydrogen, hydroxyl or an optionally substituted C$_1$-C$_4$ alkyl, C$_1$-C$_4$ alkoxy, or C$_2$-C$_4$ alkenyl; and R$_3$ is an optionally substituted aryl, heteroaryl, cycloalkyl, heterocyclyl, C$_1$-C$_{24}$ alkyl, C$_2$-C$_{20}$ alkenyl, C$_2$-C$_{20}$ alkynl, C$_1$-C$_{10}$ alkylaryl, C$_1$-C$_{10}$ arylalkyl, C$_2$-C$_{10}$ alkenylaryl, C$_2$-C$_{10}$ arylalkenyl, C$_2$-C$_{10}$ alkynylaryl or C$_2$-C$_{10}$ arylalkynyl, which optionally is interrupted by O, N, S or any combination thereof, and at least one pharmaceutically acceptable excipient, wherein a complex of gallium and the compound is prepared prior to administration of the complex to the patient.

2. The method of claim 1, wherein the compound is represented by the formula:

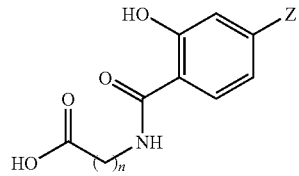

wherein Z is H or a halo and n is 3-11.

3. The method of claim 2, wherein Z is H and n is 7 or 9, or Z is chlorine and n is 3.

4. The method of claim 3, wherein n is 9.

5. The method of claim 1, wherein the gallium is radioactive.

6. The method of claim 5, wherein the gallium is gallium-67.

7. The method of claim 6, wherein gallium-67 is administered at the site of a tumor.

8. The method of claim 1, wherein the gallium is administered in the range from about 0.25 mg/kg/day to about 10 mg/kg/day.

9. A pharmaceutical composition for treatment of cancer in a patient in need of such treatment comprising, in solid form for oral administration, a therapeutically effective amount of gallium, a compound represented by structural formula I:

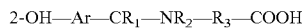
$$2\text{-OH}—Ar—CR_1—NR_2—R_3—COOH \qquad \text{I}$$

wherein 2-OH—Ar is an optionally substituted 2-hydroxyaryl;

$R_1$ is —OH or =O;

$R_2$ is hydrogen, hydroxyl or an optionally substituted $C_1$-$C_4$ alkyl, $C_1$-$C_4$ alkoxy, or $C_2$-$C_4$ alkenyl; and $R_3$ is an optionally substituted aryl, heteroaryl, cycloalkyl, heterocyclyl, $C_1$-$C_{24}$ alkyl, $C_2$-$C_{20}$ alkenyl, $C_2$-$C_{20}$ alkynl, $C_1$-$C_{10}$ alkylaryl, $C_1$-$C_{10}$ arylalkyl, $C_2$-$C_{10}$ alkenylaryl, $C_2$-$C_{10}$ arylalkenyl, $C_2$-$C_{10}$ alkynylaryl or $C_2$-$C_{10}$ arylalkynyl, which optionally is interrupted by O, N, S or any combination thereof, means to inhibit, under the acidic conditions of the stomach, dissociation of a complex formed by the gallium and the compound, and at least one pharmaceutically acceptable excipient.

10. The pharmaceutical composition of claim 9, wherein the means to inhibit dissociation of the gallium complex under the acidic conditions of the stomach comprises a hydrogel, a liposome, an enteric coating, or combinations thereof.

11. The pharmaceutical composition of claim 9, wherein the gallium is provided in the form of gallium nitrate, gallium chloride, gallium citrate or gallium sulfate.

* * * * *